United States Patent
Thesen

(10) Patent No.: US 7,421,103 B2
(45) Date of Patent: Sep. 2, 2008

(54) METHOD AND DEVICE FOR FAST PROCESSING OF MEASUREMENT DATA WITH A PLURALITY OF INDEPENDENT RANDOM SAMPLES

(75) Inventor: Stefan Thesen, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1095 days.

(21) Appl. No.: 10/720,721

(22) Filed: Nov. 24, 2003

(65) Prior Publication Data

US 2004/0162478 A1 Aug. 19, 2004

(30) Foreign Application Priority Data

Nov. 22, 2002 (DE) ............... 102 54 606

(51) Int. Cl.
*G06K 9/00* (2006.01)
*A61B 5/05* (2006.01)

(52) U.S. Cl. ...................... 382/131; 600/410
(58) Field of Classification Search ................ None
See application file for complete search history.

(56) References Cited

OTHER PUBLICATIONS

"Real-Time Functional Magnetic Resonance Imaging" by Cohen. Elsevier Science, 2001, pp. 201-220.*

Desai, et al., "Functional MRI Activity Characterization Using Response Time Shift Estimates From Curve Evolution," IEEE Transactions on Medical Imaging, Nov. 2002, pp. 1402-1412.*

Thesen et al., "Bold Magnetic Resonance Imaging in Real Time" electromedica, 2000, pp. 45-52.*

"Simultaneous Registration and Activation Detection for fMRI," Orchard et al., Magnetic Resonance in Medicine (online), Apr. 2002.

Website Printout for Statistical Parametric Mapping Software, (SPM99) (Jan. 25, 2000).

"Real-Time Multiple Linear Regression for fMRI Supported by Time-Aware Acquisition and Processing," Smyser et al., Magnetic Resonance in Medicine, vol. 45, No. 2 (2001) pp. 289-298.

"Human Brain Function," Frackowiak et al., (1997) pp. 59-84.

\* cited by examiner

*Primary Examiner*—Charles Kim
(74) *Attorney, Agent, or Firm*—Schiff Hardin LLP

(57) ABSTRACT

In a method as well as a device to process measurement data that are composed of a number of data sets with a number of independent random samples originating via temporally successive measurements, for a comparison of the time curve of each acquired random sample with the time curve of a model function using the general linear model, the required calculations are implemented data set-by-data set in a series of the data sets originating from the temporal sequence of measurements, and stored as an intermediate result, with the intermediate results of the directly preceding data set being updated with the new calculations. The comparison can be calculated efficiently and quickly, with a saving of storage space.

11 Claims, 1 Drawing Sheet

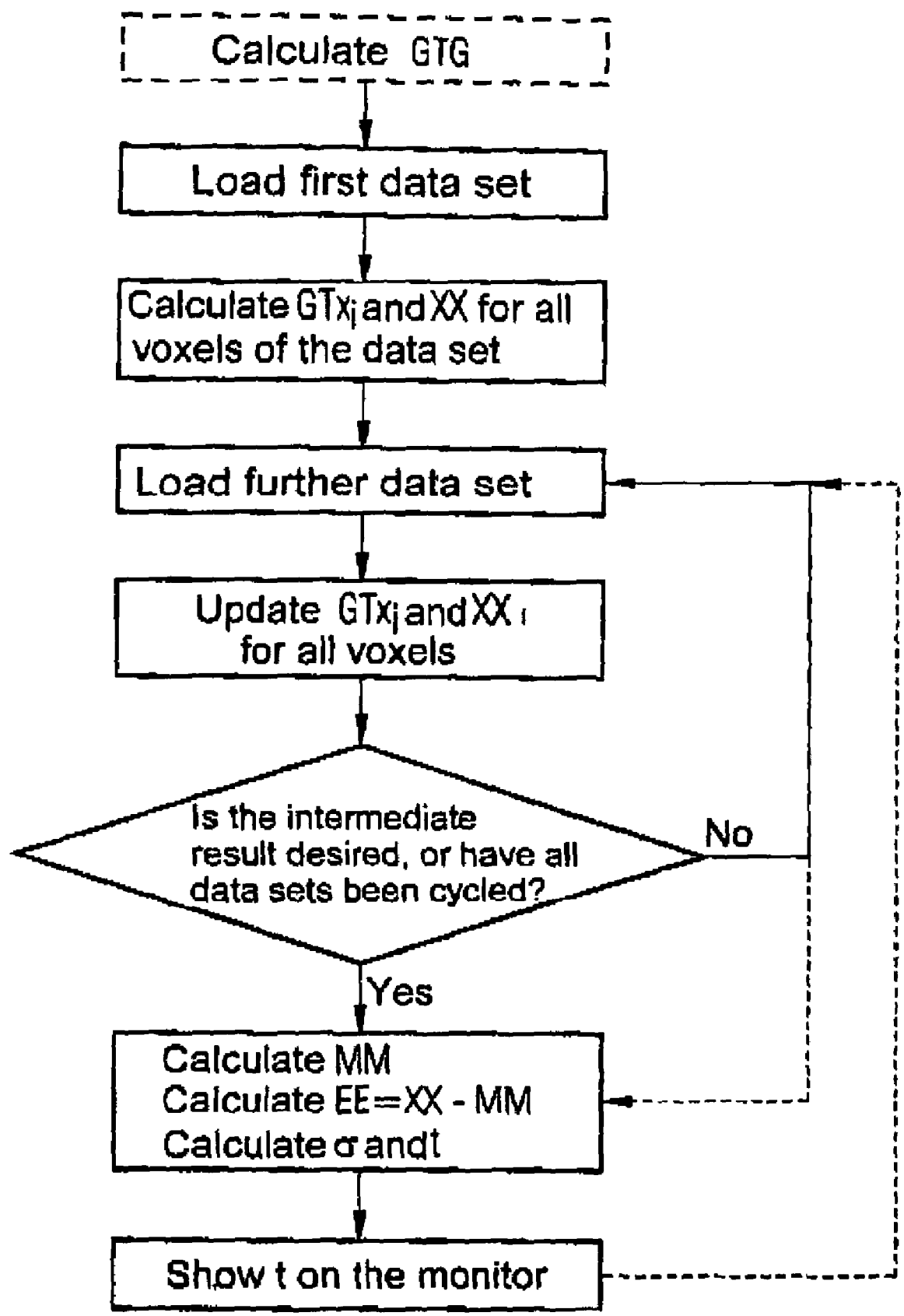

METHOD AND DEVICE FOR FAST PROCESSING OF MEASUREMENT DATA WITH A PLURALITY OF INDEPENDENT RANDOM SAMPLES

BACKGROUND OF THE INVENTION

1. Field of the Invention

The present invention concerns a method as well as a device to process measurement data formed by data sets with a number of independent random samples originating from temporally successive measurements, wherein for each independent random sample comprised in the data set, a measured time curve (that arises from the measurement data of the random sample) is compared using the general linear model with the time curve of at least one model function comprised in a model matrix, in order to test the incidence of specific patterns in the signal curve.

More particularly, the present invention concerns the processing of measurement data that are acquired from a subject volume with a measurement method of functional imaging, in particular with functional magnetic resonance tomography (fMRI), and that are composed of volume data sets originating from a number of temporally successive measurements, with, for each volume element acquired in the subject volume, a temporal signal curve that arises from measurement data of the volume element being compared with the time curve of at least one model function.

2. Description of the Prior Art

In particular in the field of medical technology and medical research, a need exists to acquire information about the brain activity in human and animal organs. The neural activity causes an increase of the blood flow in active brain areas, resulting in a decrease in the blood-deoxyhemoglobin concentration. Deoxyhemoglobin is a paramagnetic material that reduces the magnetic field homogeneity and therefore can be shown with the aid of magnetic resonance techniques, since it accelerates the $T_2^*$ signal relaxation.

Localization of brain activity is enabled by the use of a functional imaging method that measures the change of the MR signal relaxation with a time delay. The biological effective mechanism is known in the literature by the name BOLD effect (Blood Oxygen Level Dependent effect).

A fast magnetic resonance imaging enables the examination of the bold effect in vivo, dependent on activation states of the brain. In functional magnetic resonance tomography, magnetic resonance exposures of the subject volume to be examined, for example of the brain of a patient, are made in short temporal intervals. By comparison of the signal curve (measured by functional imaging) for each volume element of the subject volume with the time curve of a model function, a stimulus-specific neural activation can be detected and spatially localized. A stimulus can be, for example, a somatic sensory, acoustic, visual or olfactory stimulus, as well as a mental or motor task. The model function or the model time series specifies the expected signal change of the magnetic resonance signal in the course of neural activation. By using faster magnetic resonance techniques, such as, for example, the echo-planar method, smaller temporal intervals between the individual measurements can be realized.

In many multivariate statistical analyses, a model known as the general linear model (GLM) is used for the comparison of the measured signal curve with the time curve of a model function. With the general linear model, it is determined which linear combination of the model functions best approximates the measurement data series. Furthermore, it can be calculated for each model function how significantly the measurement data of the null hypothesis of no contribution of the respective model function contradicts the measurement data series. The general linear model is used in many fields, such as, for example, physics and sociology, to analyze measurement data. It is in particular also suitable to analyze time series as they are measured in functional magnetic resonance imaging (fMRI). By using the general linear model, it can be analyzed whether the measured time series show a pattern that corresponds to local neural activity. In addition to this pattern, however, the time series frequently also show other characteristics (such as, for example, drifts or other effects) that can likewise be modeled in the framework of the general linear model. This enables a better analysis of the measurement data than, for example, a t-test or correlation method. Thus, for example, it is also possible with the general linear model to analyze in parallel a number of effects in the brain. Group statistics about a number of test persons are also possible. Further application possibilities of the general linear model are found, for example, in "Human Brain Function" by R. Frackowiak et al., Academic Press.

In the processing of measurement data that are acquired from a subject volume with the method of functional magnetic resonance tomography, it has been necessary until now to load in the main storage of a computer the overall measurement data that comprises a number of volume data sets originating via temporally successive measurements. Subsequently, for each volume element of the measured subject volume, the signal curve or, respectively, the time series must be extracted from these measurement data and be compared with the model function. In the known implementation of the general linear model in the freely available SPM software (Wellcome Department of Cognitive Neurology; University of London; published under Gnu Public License; http://www.fil.ion.ucl.ac.uk/spm/), it is likewise necessary to load into the main storage of the computer the complete data set to be analyzed. The complete data set, in long fMRI studies—possibly also spanning a number of test persons—can include several hundred megabytes, up to gigabytes, of data. The values to be analyzed that belong to a time series of measurement data are extracted, and the general linear model is directly calculated.

This conventional data processing therefore leads to a significant main storage requirement. Since the measurement data typically exist in the storage of the computer volume by volume, corresponding to the successive measurements as a number of volume data sets, the use of this known technique also leads to very long computing times, since the individual time series must be collected together over very large ranges of the loaded data.

Presorting of the data could reduce this computing time, however this requires in turn a considerable computing time and additional storage requirements. Moreover, a sorting event can not be finished until the end of the measurement, since the time series only then exists in full. The actual calculations thus can be started only at the end of the measurement.

SUMMARY OF THE INVENTION

An object of the invention is to provide a method and a device for fast and storage-saving processing of measurement data that are formed of a number of data sets with a plurality of independent random samples, originating from temporally successive measurements, The method should in particular enable fast and storage-saving calculation of the general linear model for the case of a number of independent random samples, for example measurement data series as they occur in fMRI.

This object is achieved in accordance with the invention for the processing of measurement data that is composed of a number of data sets with a number of independent random samples, originating from temporally successive measurements.

In the following, the method and its advantages are explained (without limitation to other applications) using the processing of measurement data that are acquired from a subject volume with a measurement method of functional imaging, in particular with the method of functional magnetic resonance tomography, and that are formed of a number of volume data sets originating from temporally successive measurements. In this method, for each volume element acquired in the subject volume, a temporal signal curve is determined from the measurement data of this volume element, and at least one model function obtained in a model matrix G using the general linear model is compared with the time curve in order to test the incidence of specific characteristics or patterns in the signal curve. The present method is primarily distinguished in that calculations necessary for the comparison from the measurement data in a sequence of the of the data sets, or volume data sets originating from the time sequence of the measurements, are implemented for all relevant measurement data of a volume data set and are stored as intermediate results. The intermediate results from the directly preceding volume data set are updated with the new calculations, such that at any time intermediate results can be calculated, and after the one-time cycle of all volume data sets an end result exists that allows an assertion about the incidence of the characteristics or patterns in the signal curve. The square of an error vector necessary for the end result is obtained from the difference of the square of a measurement value vector formed from the measurement data and the square of a model vector calculated from the model function.

In contrast to the known method of the prior art, in the present method the measurement data are not cycled for the comparison according to time series or volume elements, but rather volume-by-volume. After implementation of the calculations with the measurement data and storage of an intermediate result, each volume data set can again be discarded from the main storage of the data processing system. For this reason, it is no longer necessary to load the entirety of the measurement data, meaning all volume data sets of the measurements, into the working storage of the data processing system. Rather, it is sufficient merely to load the measurement data of an individual volume data set. For this reason, the present method can be implemented efficiently and quickly, saving much storage space, since respectively only small data ranges must be accessed in the calculation. The volume data sets must hereby overall only be cycled once, volume-by-volume.

In the solution of the above object, consideration has been made that the present computer architecture is very slow in the calculation of large data ranges, in particular in the gigabyte range, however it can implement small data ranges with noticeably higher speed. With the present method, in which only small data ranges are always used for calculation volume-by-volume, a noticeably higher calculation speed thus can be achieved. Furthermore, the storage requirement that is necessary for the processing of the data is no longer dependent in the present method on the number of the volume data sets (meaning the number of the measurements), but rather is substantially dependent only on the size of the measured subject volume. A further advantage of the present method is that all calculations can already be implemented during the measurement. Real-time applications as well as the display of an always-current Intermediate result are also thereby possible. Furthermore, the model function in the present method can first be defined during the measurement, and does not have to be known a priori. The method can be implemented in parallel very efficiently, such that a number of computers or processors can be used to accelerate the calculations.

The present method is explained again as an example using an fMRI data set, however it can naturally also be applied in the same manner to data sets of other functional imaging methods or other measurement data with independent random samples, corresponding to the measurement data series of the individual volume elements in the fMRI.

In functional magnetic resonance tomography, the subject volume, for example the brain of a test person, is repeatedly sampled three dimensionally at small temporal intervals, and from the raw data the desired image information is reconstructed in voxels, meaning volume elements, via a Fourier transformation. A corresponding measurement value is hereby associated with each volume element. The overall measurement is composed of a number of volume data sets that form the measurement data of the measurements temporally following in quick succession. Each volume data set is composed of the measurement data, acquired at a specific point in time, of the individual voxel of the subject volume. For the recognition of activation states of the measured brain, the signal curves resulting from the temporally successive measurement values of each voxel are compared in order to be able to establish the degree of a coincidence. Due to the use the widespread general linear model (GLM) according to the present method, this comparison can be implemented with a great saving of storage space. In the general linear model, a design matrix or model matrix G is generated with one or more model functions from which, in connection with the measurement data of each volume element, values (in particular a t-statistic) can be calculated, from which the degree of coincidence with the model functions of the model matrix is visible.

In the implementation of the method using the general linear model, the volume data sets of the measurements are only cycled once. After cycling each data set with the thereby-implemented calculations, an intermediate result is stored that is updated upon cycling of the directly ensuing volume data set via the new calculations—due to the new measurement data—and is stored as an intermediate result of this new volume data set. By this volume-by-volume updating of the intermediate results, it is possible to obtain a result at any time from which, for example, the t-statistic can be calculated. The square of the error vector required for this is obtained from the difference of the square of the measurement value vector formed from the measurement data and the square of the model vector calculated from the model function. This simple calculation is possible since the error vector and the model vector are perpendicular to one another, due to the least squares condition, and when added yield the measurement value vector. For the calculation of the square of the error vector, therefore only the length of the measurement value vector and the length of the model vector must be determined. The square of the error vector can then be calculated by the set of Pythagoras. The model vector thereby comprises the values calculated from the model function that should approach as best possible the measurement values.

The present method is thus based on an update event in which the volume data sets are only cycled once. At the end of the update event, the data necessary for the calculation of the t-statistic from the measurement values are all available.

In one embodiment, the update event, the cycle through the volume data sets, can ensue simultaneously with the measurement, with the respective calculation being implemented directly after obtaining a new volume data set. In this embodiment, the update event is therefore already finished with the end of the data acquisition.

Given sufficient computing speed, a real-time application of the present method is also possible, in that during the measurement regular intermediate evaluations are undertaken in which the update event is interrupted and the calculation of the t-statistic is implemented. The update event can subsequently be continued for the volume data sets measured in the following time period.

In the present method, buffers are necessary that, for the use of the general linear model, must exhibit a size that satisfy the following equation:

Size of the storage=number of the volume elements×
(2×number of the model functions+2)×4 bytes.

The four bytes as a storage space for a floating-point number of the float data type have turned out to be sufficient for the implementation of the present method. The number of the volume elements can, for example, comprise 64×64×32 values. This corresponds to the size of a typical sample data set of a subject volume in functional magnetic resonance tomography.

The present method can be used, for example, in a computer of a magnetic resonance scanner, such that a fast post-processing of fMRI data is possible. Via suitable implementation of the method, the representation of the comparison results can also ensue in real-time, as long as the data sets do not comprise too many volume elements and the number of the model functions is not chosen too high. In particular, the calculation in real-time is not limited by the number of the volume data sets, since the calculation time is constant, independent of the number of the already added data sets.

DESCRIPTION OF THE DRAWINGS

The FIGURE is a flow chart of an exemplary embodiment of the inventive method.

DESCRIPTION OF THE PREFERRED EMBODIMENTS

In the inventive method, first the model matrix G is defined, that is composed of a number of columns with model functions. The time series in the present invention merely contains twenty measurements. For each volume element, twenty measurement values $x_m$ are thereby obtained, whereby $m=0\ldots max-1$ and $max=20$. As a model matrix, a matrix with five model functions is selected, meaning a matrix with five columns and twenty rows.

In the first column is the model function of the neural activation that for example can be formed by:

$$G=(11111000110011001100)^T$$

In the second column, a constant ration is represented in the measurement data:

$$G_{m,1}=1.$$

The further three columns serve as high-pass filters, meaning they model slow drifts during the measurement on a cosine basis [cosinus basis]. These model functions can, for example, be selected as $$G_{m,2} = \cos\left(\frac{\pi \cdot i}{max}\right) \quad G_{m,3} = \cos\left(\frac{2\cdot\pi\cdot i}{max}\right) \quad G_{m,4} = \cos\left(\frac{3\cdot\pi\cdot i}{max}\right)$$

The model matrix $G_{mj}$ thus comprises the collection of model functions that should be adapted to the measurement data $x_m$.

In the implementation of the comparison of the measurement data with these model functions, a least-squares estimate of the parameters is implemented. A vector b is thereby defined, from which the coincidence of the measurement data series with individual model functions of the model matrix is visible. This vector b is calculated in the following manner:

$$B=(G^T \cdot G)^{-1} \cdot G^T x.$$

The vector b in the present example is composed of five values, corresponding to the number of the columns or model functions of the model matrix. Each value represents how the corresponding model function must be scaled in order to approximate the measurement data.

Next, an error consideration must be implemented in order to obtain an assertion about the quality of the estimate. For this, the value σ is calculated that results in the following manner:

$$\sigma := \sqrt{\frac{e \cdot e}{max - rang(G)}}$$

whereby e=G·b−x.

Finally, what is known, as the t-statistic is calculated by, for each volume element, obtaining a value t having a magnitude that is a measure for the degree of the coincidence of the measurement data series represented with the considered model function. In functional imaging methods, such as functional magnetic resonance tomography explained here as an example, it is typical to visualize these t-values. For the calculation of the t-statistic, a contrast must first be defined that specifies the model function of interest. In the present case, this contrast c can be given by the following value: $c=(10000)^T$.

The t-value then results in the following manner:

$$t := \frac{c \cdot b}{\sqrt{\sigma^2 \cdot c \cdot [(G^T \cdot G)^{-1} \cdot c]}}$$

In the implementations implemented until now in the prior art, the time series of each voxel is extracted in succession from the fMRI data set and undergoes the analysis above. However, for this it is necessary for the calculation to simultaneously load all measurement data of all volume data sets into the working storage of a computer. In addition to the high storage space requirement, this also leads to a correspondingly slow calculation speed.

In contrast to this, with the present invention as shown in the FIGURE in an embodiment, both the storage space requirement can be reduced and the calculation speed can be increased. In the inventive method, in the update event the fMRI data set is cycled volume by volume, meaning one volume data set after the other, and the respective calculations are implemented in each volume data set for each volume element.

This can ensue in the following manner. In the update event, in which all volume data sets are cycled once, the vector GTx is updated for each new volume data set and each voxel, whereby respectively only the new line of the model matrix and the now measurement value are accessed:

$$GTx_l = GTx_l + G_{m,l}x_m$$

GTX hereby designates the vector $G^T \cdot x$. This calculation is implemented in each new volume data set for each volume element, and can also be distributed voxel by voxel onto various computers or, respectively, processors. The value obtained from the preceding volume data set for the Individual components of the vector GTx is hereby updated. Of course, this value must be set to zero in the implementation of the calculation for the very first volume data set.

The implementation of this calculation for each volume data set implies that a sufficient buffer must be present for the respective interim value of GTx that corresponding to the number of the volume elements in the volume data set multiplied by the number of the model functions in the model matrix.

Furthermore, in this cycle of the data sets for each new volume data set and each voxel, the square XX of the measurement value vector us updated, with only the new measurement value is accessed:

$$XX = XX + (x_m)^2$$

At the same time, in this cycle the matrix GTG (corresponds to $G^T \cdot G$) can also be update by following instruction:

$$GTG_{i,k} = GTG_{i,k} + G_{m,i} \cdot G_{m,k}.$$

Naturally, this calculation (since it involves no measurement data) also can be implemented in a step before the cycle, as indicated dashed in the FIGURE, or after this cycle. However, in a model matrix whose model functions are first defined or changed in the course of the measurement, or when intermediate results should be calculated, the implementation is necessary according to the above instruction, meaning the volume-by-volume calculation during the cycle.

After obtaining the matrix GTG, this is inverted. This can ensue, for example, by means of an LU decomposition, since this matrix is a small, symmetric, real matrix, in the present example a 5×5 matrix. Naturally, however, other inversion algorithms can also be used. Finally, the vector b is calculated for each volume element, which results by $$b = GTG^{-1} \cdot GTx$$

After implementation of the update event, the values for the vector b and the pseudo-inverse $(G^T \cdot G)^{-1}$ are thus established.

To calculate the value for the square of the error vector e (designated in the following as EE), used is made of the fact that the part of the measurement value vector (designated as model vector M) representable via the model, and the vector E, are perpendicular to one another, due to the least squares condition, and when added result in the measurement value vector X. Thus only the length of the measurement value vector and the length of the model vector must be determined in order to be able to calculate from this the set of Pythagoras EE. Thus:

$$M = G \cdot b \quad \text{Model matrix} = M \cdot M$$

$$MM = (G \cdot b) \cdot (G \cdot b) = q \cdot q = \sum_{i=0}^{max-1} q_i \cdot q_i$$

with:

$$q_i = \sum_{j=0}^{sp-1} G_{i,j} \cdot b_j$$

The use of which results in:

$$MM = \sum_{i=0}^{max-1} \sum_{j=0}^{sp-1} G_{i,j} \cdot b_j \cdot \sum_{k=0}^{sp-1} G_{i,k} \cdot b_k$$

$$= \left[ \sum_{i=0}^{max-1} \left[ \sum_{j=0}^{sp-1} \sum_{i=0}^{sp-1} (G_{i,j}, G_{i,k}) \cdot b_j \cdot b_k \right] \right]$$

The inner parentheses represent the matrix $GTG^{-1}$ that was already calculated. Thus;

$$MM = MM + GTG_{j,k} \cdot b_j \cdot b_k$$

such that MM can be calculated quickly, and leads directly to EE:

$$EE = XX - MM.$$

For the previously implemented calculations:

$$i = 0 \ldots sp-1$$

$$k = 0 \ldots sp-1$$

$$j = 0 \ldots sp-1$$

$$m = 0 \ldots \max-1$$

whereby max corresponds to the number of the measurements or, respectively, volume data sets and sp corresponds to the columns of the model matrix G.

After each addition of a volume data set, or also at the end of the measurement, the t-statistic cannot be calculated for this comparison. In the present example, a scaling factor Scale is hereby first calculated according to the following instruction:

$$\text{Scale} = \text{Scale} + \text{contrast increase} \cdot GTG_{i,j} \cdot c_j.$$

whereby c corresponds to the contrast vector.

This calculation is implemented for each volume element. Furthermore, the $\sigma^2$ is calculated for each volume element, which results according to the following known instruction:

$$\sigma^2 := \frac{UEE}{\max - rang(G)}.$$

From this value, what is known as the t-value can be separately calculated for each voxel by $$t + c_i \cdot b_i.$$

This t is finally divided again by Eq, in order to obtain for each voxel the final t-value that, for example, can be visualized by superimposition on a typical magnetic resonance exposure of the subject volume. The final calculations can likewise by distributed voxel by voxel to different computers or, respectively, processors calculating in parallel, in order to accelerate the calculation.

Furthermore, the FIGURE shows the possibility, indicated by the dashed arrows, to calculate and to output an intermediate result during the cycle of the data sets.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to process measurement data comprised of a plurality of data sets with a plurality of independent random samples originating via temporally successive measurements comprising the steps of:

for each independent random sample in the data set, comparing a measured time curve arising from measurement data x of the random sample, using the general linear model, with a time curve of at least one model function of a model matrix G, to test for incidence of specific characteristics in the measured time curve;

implementing individual calculations for the comparison from the measurement data in a sequence of the data sets, or volume data sets originating from the time sequence of the measurements, for all relevant measurement data of a volume data set and storing said calculations as intermediate results;

updating the intermediate results from a directly preceding volume data set with new calculations, such that at any time intermediate results can be calculated, and after a one-time cycle of all volume data sets an end result exists from which an assertion about the incidence of the characteristics in the signal curve is derived; and calculating, in the cycle of the data sets, for each data set m and each random sample, vector elements $$GTx_i = GTx_i^{old} + G_{m,i} \cdot G_{m,k}$$

and the square of a measurement value vector $$XX = XX^{old} + (x_m)^2$$

from the calculated vector elements $GTx_i^{old}$ and the square of the vector $XX^{old}$ of the directly preceding data set, and for the subsequent data set and storing said squares as an intermediate result, whereby m=0 ... max−1, i=0 ... sp−1, k=0 ... sp−1, sp corresponds to of the number of the columns of the model matrix G, and max corresponds to the total number of the data sets, and subsequently calculating the square of a model vector $$MM = MM^{old} + GTG_{j,k} \cdot b_j \cdot b_k$$

and the square of an error vector $$EE = XX - MM$$

whereby j=0 ... sp−1 and $b_j$, $b_k$ are vector elements of the vector $b = GTG^{-1} \cdot GTx$ that are calculated in an intermediate step.

2. A method as claimed in claim 1, comprising calculating in the cycle of the data sets, furthermore for each data set m the matrix elements $$GTG_{i,k} = GTG_{i,k}^{old} + G_{m,i} \cdot G_{m,k}$$

from the calculated vector elements $GTG_{i,k}^{old}$ of the directly preceding data set, and for the subsequent data set are stored as an intermediate result.

3. A method as claimed in claim 1, comprising before or after the cycle of the data sets, calculating the matrix elements $GTG_{i,k}$ from the model matrix G in a step.

4. A method as claimed in claim 1 comprising, after an end of the cycle, calculating a t-value from the calculated values for each random sample.

5. A method as claimed in claim 1 comprising for said calculations for said comparison, loading only one data set into a working storage of a data processing system, and after the calculations discarding the loaded data set.

6. A method as claimed in claim 1 comprising cycling the data sets in parallel with the measurements.

7. A method as claimed in claim 6, comprising interrupting the cycle of the data sets after a predeterminable number of measurements, and present a current result of the measurements, and after this interruption continuing the cycle.

8. A method as claimed in claim 1 comprising acquiring said data sets from a subject volume by functional imaging, with the data sets originating from temporally successive measurements representing volume data sets, and with the time curve for an independent random sample comprised in the data set corresponding to the temporal signal curve of a volume element acquired in the subject volume.

9. A data acquisition and processing arrangement comprising:

a data acquisition device configured to obtain a plurality of data sets with a plurality of random samples originating in temporally successive measurements; and a processor and a working memory connected to said processor, said processor being configured to process said data sets by, for each independent random sample in the data set, comparing a measured time curve arising from measurement data x of the random sample, using the general linear model, with a time curve of at least one model function of a model matrix G, to test for incidence of specific characteristics in the measured time curve, implementing individual calculations for the comparison from the measurement data in a sequence of the data sets, or volume data sets originating from the time sequence of the measurements, for all relevant measurement data of a volume data set and storing said calculations as intermediate results, updating the intermediate results from a directly preceding volume data set with new calculations, such that at any time intermediate results can be calculated, and after a one-time cycle of all volume data sets an end result exists from which an assertion about the incidence of the characteristics in the signal curve is derived, and calculating, in the cycle of the data sets, for each data set m and each random sample, vector elements $$GTx_i = GTx_i^{old} + G_{m,i} \cdot G_{m,k}$$

and the square of a measurement value vector $$XX = XX^{old} + (x_m)^2$$

from the calculated vector elements $GTx_i^{old}$ and the square of the vector $XX^{old}$ of the directly preceding data set, and for the subsequent data set and storing said squares as an intermediate result, whereby m=0 ... max−1, i=0 ... sp−1, k=0 ... sp−1, sp corresponds to of the number of the columns of the model matrix G, and max corresponds to the total number of the data sets, and subsequently calculating the square of a model vector $$MM = MM^{old} + GTG_{j,k} \cdot b_j \cdot b_k$$

and the square of an error vector $$EE = XX - MM$$

whereby j=0 ... sp−1 and $b_j$, $b_k$ are vector elements of the vector $b = GTG^{-1} \cdot GTx$ that are calculated in an intermediate step.

10. A device as claimed in claim 9 wherein said data acquisition device is a magnetic resonance system.

11. A device as claimed in claim 10 wherein said data acquisition device is a functional magnetic resonance system.

* * * * *